United States Patent [19]

Osugi et al.

[11] 4,054,609
[45] Oct. 18, 1977

[54] PROCESS FOR THE PREPARATION FOR FORMALDEHYDE

[75] Inventors: Minoru Osugi; Takako Uchiyama, both of Niigata, Japan

[73] Assignee: Mitsubishi Gas Chemical Company, Inc., Tokyo, Japan

[21] Appl. No.: 697,255

[22] Filed: June 17, 1976

[30] Foreign Application Priority Data

June 20, 1975 Japan .................................. 50-75397

[51] Int. Cl.$^2$ ............................................ C07C 47/04
[52] U.S. Cl. .................. 260/603 R; 260/606
[58] Field of Search ............ 260/603 R, 603 HF, 606, 260/600, 603 A

[56] References Cited

U.S. PATENT DOCUMENTS 2,939,883  6/1960  Punderson ........................ 260/603 R
3,778,477  12/1973  Mueller et al. ..................... 260/603

Primary Examiner—James O. Thomas, Jr.
Assistant Examiner—W. B. Lone

[57] ABSTRACT

A process for the preparation of formaldehyde by subjecting methanol to dehydrogenation in the presence of a catalyst consisting of copper, zinc and selenium as metallic components.

6 Claims, No Drawings

PROCESS FOR THE PREPARATION FOR FORMALDEHYDE

The present invention relates to a process for the preparation of formaldehyde by dehydrogenation of methanol. More particularly, it relates to a process for the preparation of formaldehyde by the dehydrogenation of methanol in the presence of copper, zinc and selenium as catalyst components.

Catalytic oxidative dehydrogenation, catalytic oxidation and the like are generally known as a commercially available process for the preparation of formaldehyde. According to these prior art processes, formaldehyde is generally obtained as an aqueous solution whose concentration is found to be at most 40% by weight.

These aqueous formaldehyde solutions are very unstable, and so they are not satisfactory in both quality and handling. For instance, precipitation of paraformaldehyde during storage and transportation, as well as formation of formic acid by a side reaction, may befrequently observed. Further, paraformaldehyde which is obtained by the concentration of the aqueous formaldehyde solution has a defect that its solubility decreases several days after the preparation although the paraformaldehyde obtained just after the preparation is comparatively well soluble in water, an alcohol, etc. in a few days after the preparation.

On the other hand, there have been proposed many methods for the production of formaldehyde by the so-called dehydrogenation of methanol. For example, a method using a catalyst consisting of copper, silver and silicon (see U.S. Pat. No. 2,939,883), a method using a catalyst having metallic zinc adhered on the surface of a metallic copper support (Japanese Patent Publication No. 11,853/1966), a method using fused zinc, gallium, indium or aluminum or an alloy thereof (Japanese Patent Publication No. 19,251/1972), and a method contacting methanol with fused zinc containing carbon or a zinc alloy containing carbon (Japanese Patent Laid Open No. 97,808/1973) have been proposed. However, even these methods have common serious disadvantages in that the life of their catalysts and the conversion obtained are so poor as to make these methods not industrially acceptable.

We also proposed several processes for the preparation of formaldehyde in a high yield by using a novel catalyst: a process wherein a catalyst prepared from copper, zinc and sulfur is used (Japanese Patent Application No. 63,984/1974) and a process wherein sulfur is fed in gaseous state in order to prevent deterioration of the catalyst (Japanese Patent Application No. 148,390/1974). These processes are superior to the prior art processes in that the catalysts have high activity; but the sulfur undesirably entrains into the reaction product or the exit gas in accordance with these process because of using sulfur as the catalyst.

Accordingly, it is an object of the present invention to provide a novel process for the preparation of formaldehyde.

Another object of the present invention is to provide a process for the preparation of formaldehyde by dehydrogenation of methanol by using a catalyst without any sulfur-exhausting problem.

A further object of the present invention is to provide a process for the preparation of formaldehyde which is excellent in both thermal stability and storage stability. A still further object of the present invention is to provide an excellent catalyst for the preparation of formaldehyde.

In accordance with the present invention, these objects can be accomplished by a process for the preparation of formaldehyde comprising subjecting methanol to dehydrogenation in the presence of a ternary metal catalyst comprising copper, zinc and selenium.

The atomic ratio of these metals constituting the catalyst of the present invention may be as follows: copper/zinc/selenium 1:0.01–0.5:0.01–0.5, preferably 1:0.1–0.4:0.1–0.4, provided the amount of selenium preferably should not exceed that of zinc.

The catalyst used in the present invention may be prepared by any one of conventional procedures known to those skilled in the art, for example, precipitation method, thermal decomposition method, or deposition and drying method. Any of these procedures may be properly selected based on the raw material to be used.

The raw materials for the catalyst in the present invention include a copper salt of a mineral acid such as copper nitrate, copper chloride, copper sulfate and copper sulfite, etc., copper hydroxide, copper oxide, basic copper cabonate, metallic copper, etc. as a copper source; a zinc salt of a mineral acid such as zinc nitrate, zinc chloride, zinc sulfate and zinc sulfite, etc., zinc hydroxide, zinc oxide, metallic zinc as a zinc source; and selenic acid, selenious acid, selenium oxide, metallic selenium, etc. as a selenium source. Further, zinc selenide, zinc selenate, zinc selenite, etc. may be used as both zinc and selenium sources and copper selenide may be used as both copper and selenium sources.

The raw material for the catalyst may be in the form of either powder or grains, etc.

The above raw materials may be formed to a particle having a desired shape which may be tablet, sphere or the like and the average diameter of the particles thus formed would be more than 1 mm, preferably 2 to 5 mm. The catalyst particles are then reduced in a reductive atmosphere, for example, in two steps, first at a temperature of 100° to 300° C, preferably 150° to 250° C for more than 0.2 hour, preferably 0.5 to 1 hour and then at the temperature of 500°–750° C, preferably 600°–700° C for more than 0.1 hour, preferably 0.5–1 hour.

The reaction temperature for the present invention may be 500° to 750° C, preferably 600° to 700° C in a catalyst bed. If it is below 500° C, conversion decreases, and if it is higher than 750° C, yield decreases. This reaction temperature is a temperature conventionally employed in the art.

The dehydrogenation reaction in the present invention, generally, may be carried out under atmospheric pressure. However, it may be carried out under reduced or superatmospheric pressure, if desired.

Methanol is generally fed in vapor form together with hydrogen gas to the catalyst bed. Methanol may be preferably fed in an amount of 0.2 to 0.7 mol/hr per 20 ml of the catalyst. The feed amount of less than 0.2 ml/hr is not practical, whereas that of more than 0.7 mol/hr shows decreased conversion of methanol.

According to the present invention, the product obtained contains 30 to 85% by weight of formaldehyde, 0 to 2% by weight of water and the balance of methanol. It is to be appreciated that formaldehyde can be obtained in a high yield, with a very small water content.

The product obtained in accordance with the present invention has quite a different property from an aqueous formaldehyde solution or paraformaldehyde prepared by any conventional method. That is to say, when the formaldehyde concentration in the product obtained by the present invention is not more than 70% by weight, the product is a clear liquid at an ordinary temperature and does not show any appreciable solid precipitation, even if it is left alone at an ordinary temperature for a long period of three months or more. When the formaldehyde concentration is more than 70% by weight, the product is a white solid at ambient temperature, but it melts easily by heating to form a clear liquid, and then it becomes solid again on cooling. Even if such melting by heating and solidification by cooling are repeated, the fusion temperature does not change. For example, the product in the present invention containing 73.0% by weight of formaldehyde, 25.9% by weight of methanol and 1.1% by weight of water is solid at ordinary temperature, but it becomes a clear liquid by heating at a temperature of 30° to 35° C and it solidifies again by cooling. Such a heating-cooling cycle is repeated once a day for 30 days, but the melting temperature did not change. This fact shows that the product obtained by the present invention is more stable compared with those obtained by the prior art processes.

The present invention is illustrated in detail by the following examples, in which conversion and yield are defined as follows:

$$\text{Conversion (\%)} = \frac{\text{Methanol reacted (mol)}}{\text{Methanol fed (mol)}} \times 100$$

$$\text{Yield (\%)} = \frac{\text{Formaldehyde produced (mol)}}{\text{Methanol fed (mol)}} \times 100$$

EXAMPLE 1

Each aliquot, 50.0 g of cupric oxide, 7.0 g of selenium dioxide and 7.0 g of zinc oxide, was ground and mixed thoroughly in a kneader. Thereto, 30 ml of water was added to obtain a paste, which was in turn formed into tablets each being 3 mm in diameter and 3 mm in height. The tablets thus obtained were reduced in a hydrogen gas stream at a temperature of 200° C and then at a temperature of 650° C respectively for 30 minutes to obtain a catalyst.

20 ml of the catalyst thus obtained was packed in a quartz glass-made tubular reactor having an inner diameter of 21 mm, and 15.0 g (0.468 mol)/hr of methanol vapor and an equimolar amount of hydrogen gas were fed thereto continuously from one end of the reactor and subjected to reaction at a catalyst bed temperature of 650° C. Conversion of 78.1% and yield of 66.0% were obtained. The catalytic activity was maintained for more than 50 hours. Composition of the product is 73.0% by weight of formaldehyde, 1.1% by weight of water and 25.9% by weight of methanol in the condensed phase and 87.3% by volume of hydrogen, 9.1% by volume of carbon monoxide, 2.7% by volume of methane and 0.9% by weight of carbon dioxide in the gas phase. The gas phase constitutes 15% by weight on total weight basis while the condensed phase comprises 85% by weight.

The amount and composition of the gas phase is nearly the same all in the following examples.

EXAMPLE 2

A catalyst was prepared from 40.0 g of cupric oxide and 14.5 g of zinc selenide as raw materials in the same manner as in EXAMPLE 1. The reaction was carried out by using the catalyst under the same conditions as in EXAMPLE 1 thereby to obtain a conversion of 73.8% and a yield of 64.5%. The catalytic activity was maintained over more than 55 hours. Further, the composition of the product in the condensed phase was 69.3% by weight of formaldehyde, 0.7% by weight of water and 30.0% by weight of methanol.

EXAMPLE 3

A catalyst was prepared from 50.0 g of powdered copper and 60.6 g of zinc selenite as raw materials in the same manner as in EXAMPLE 1. The reaction was carried out under the same conditions as in EXAMPLE 1 to obtain a conversion of 69.0% and yield of 62.1%. The catalytic activity was maintained over more than 50 hours. The composition of the product in the condensed phase was 64.9% by weight of formaldehyde, 0.5% by weight of water and 34.6% by weight of methanol.

EXAMPLE 4

A catalyst was prepared from 50.0 g of cupric hydroxide anhydride and 2.0 g of zinc selenide as raw materials in the same manner as in EXAMPLE 1. The reaction was carried out under the same conditions as in EXAMPLE 1 to obtain a conversion of 65.5% and a yield of 59.4%. The catalytic activity was maintained over more than 35 hours. Composition of the product in the condensed phase was 61.5% by weight of formaldehyde 0.5% by weight of water and 38.0% by weight of methanol.

EXAMPLE 5

Copper nitrate trihydrate (242.0 g) and zinc nitrate hexahydrate (40.7 g) were dissolved in 1500 ml of water to obtain nitrate solution. Separately, sodium hydroxide (91.0 g) was dissolved in 500 ml of water to obtain an aqueous sodium hydroxide solution and the aqueous solution was added dropwise to the nitrate solution over 1 hour. The precipitate thus obtained was separated by filtration and then dispersed into about 1500 ml of water. The resulting dispersion was vigorously stirred for 15 minutes and was filtered with stirring to obtain a cake. Such washing procedure as above was repeated six times. Selenium dioxide (11.1 g) was added to the cake thus obtained and the cake was crushed, mixed, formed and reduced in the same manner as in EXAMPLE 1 to obtain a catalyst.

The reaction was carried at a catalyst bed temperature of 680° C by using the catalyst thus obtained under the same conditions as in EXAMPLE 1 to obtain a conversion of 88.5% and a yield of 57.6%. The catalytic activity was maintained over more than 50 hours. The composition of the product in the condensed phase was formaldehyde (81.4% by weight), water (1.3% by weight) and methanol (17.3% by weight).

COMPARATIVE EXAMPLE 1

A catalyst was prepared in the same manner as in EXAMPLE 1 but without using selenium dioxide. The reaction was carried out using the catalyst under the same conditions as in EXAMPLE 1 to obtain a conversion of 98.2% and a yield of 12.2%. The yield was considerably lower than those of the EXAMPLES.

COMPARATIVE EXAMPLE 2

A catalyst was prepared in the same manner as in EXAMPLE 1 but without using zinc oxide. The reaction was carried out by using the catalyst under the same conditions as in EXAMPLE 1 to obtain a conversion of about 60% and a yield of about 50%, after 1 to 2 hours from the start of the reaction. The catalytic activity, however, deteriorated gradually, and conversion and yield decreased respectively to 40% and 35% after 5 hours from the start.

EXAMPLE 6

EXAMPLE 1 was repeated, except that the reaction was carried out at a catalyst bed temperature of 700° C. in place of the catalyst bed temperature of 650° C., thereby to obtain a conversion of 90.2% and a yield of 55.1%. The catalytic activity was maintained over more than 50 hours. Further, the composition of the product in the condensed phase was 83.6% by weight of formaldehyde, 0.6% by weight of water and 15.8% by weight of methanol.

EXAMPLE 7

EXAMPLE 1 was repeated, except that the reaction was carried out at a catalyst bed temperature of 600° C. in place of the catalyst bed temperature of 650° C., thereby to obtain a conversion of 60.2% and a yield of 55.3%. The catalytic activity was maintained over more than 70 hours. Further, the composition of the product in the condensed phase was 55.5% by weight of formaldehyde, 1.9% by weight of water and 42.6% by weight of methanol.

EXAMPLE 8

A catalyst was prepared from 50.0 g of cupric oxide, 5.0 g of zinc hydroxide and 5.6 g of selenium dioxide as raw materials in the same manner as in EXAMPLE 1. The reaction was carried out by using the catalyst under the same conditions as in EXAMPLE 1 thereby to obtain a conversion of 93.4% and a yield of 49.3%. The catalytic activity was maintained over more than 50 hours. Further, the composition of the product in the condensed phase was 87.2% by weight of formaldehyde, 0.4% by weight of water and 12.4% by weight of methanol.

EXAMPLE 9

A catalyst was prepared from 50.0 g of cupric oxide, 15.0 g of zinc oxide and 14.4 g of selenium powder as raw materials in the same manner as in EXAMPLE 1. The reaction was carried out by using the catalyst under the same conditions as in EXAMPLE 1 thereby to obtain a conversion of 53.7% and a yield of 48.8%. The catalytic activity was maintained over more than 60 hours. Further, the composition of the product in the condensed phase was 48.8% by weight of formaldehyde, 1.9% by weight of water and 49.3% by weight of methanol.

What we claim is:

1. A process for the preparation of formaldehyde, comprising subjecting methanol in the vapor phase to dehydrogenation in the presence of a catalytically effective amount of a catalyst consisting of copper, zinc and selenium as catalyst components at a temperature of 500° to 750° C. wherein the atomic ratio of said catalyst components is 1:0.1–0.5 : 0.01–0.5 for Cu:Zn:Se.

2. A process according to claim 1, wherein the dehydrogenation was carried out at a temperature of 600° to 700° C.

3. A process according to claim 1, wherein the catalyst has the copper/zinc/selenium atomic ratio of 1:0.1–0.4:0.1–0.4.

4. A process according to claim 1, wherein the methanol is fed together with hydrogen gas to a catalyst bed.

5. A process according to claim 1, wherein the methanol is fed to a catalyst bed in an amount of 0.2 to 0.7 mol/hr per 20 ml of the catalyst.

6. A process according to claim 5, wherein the methanol is fed with hydrogen gas, to a catalyst bed.

* * * * *